United States Patent
Hojo et al.

(10) Patent No.: US 10,188,821 B2
(45) Date of Patent: Jan. 29, 2019

(54) OXYGEN CONCENTRATION DEVICE

(71) Applicant: Teijin Pharma Limited, Tokyo (JP)

(72) Inventors: Maki Hojo, Tokyo (JP); Katsushi Fujimoto, Tokyo (JP)

(73) Assignee: Teijin Pharma Limited, Tokyo (JP)

(*) Notice: Subject to any disclaimer, the term of this patent is extended or adjusted under 35 U.S.C. 154(b) by 144 days.

(21) Appl. No.: 15/508,564

(22) PCT Filed: Sep. 17, 2015

(86) PCT No.: PCT/JP2015/077408
§ 371 (c)(1),
(2) Date: Mar. 3, 2017

(87) PCT Pub. No.: WO2016/047805
PCT Pub. Date: Mar. 31, 2016

(65) Prior Publication Data
US 2017/0274171 A1 Sep. 28, 2017

(30) Foreign Application Priority Data

Sep. 25, 2014 (JP) .................. 2014-195031

(51) Int. Cl.
*B01D 53/04* (2006.01)
*A61M 16/10* (2006.01)
*B01D 53/047* (2006.01)
*C01B 13/02* (2006.01)
*A61M 16/20* (2006.01)
*B01J 20/34* (2006.01)

(52) U.S. Cl.
CPC ........ *A61M 16/101* (2014.02); *A61M 16/203* (2014.02); *B01D 53/047* (2013.01);
(Continued)

(58) Field of Classification Search
CPC .............. A61M 16/101; A61M 16/203; A61M 2202/0208; A61M 2202/0007;
(Continued)

(56) References Cited

U.S. PATENT DOCUMENTS 3,280,536 A * 10/1966 Berlin ................... A61G 10/04
  95/105
4,925,461 A    5/1990 Gemba et al.
(Continued)

FOREIGN PATENT DOCUMENTS

JP    02-174912 A    7/1990
JP    2008-214151 A    9/2008
(Continued)

OTHER PUBLICATIONS

Machine Translation of JP 2011-020566 (Original document with English Abstract submitted on Mar. 3, 2017).
(Continued)

*Primary Examiner* — Frank M Lawrence, Jr.
(74) *Attorney, Agent, or Firm* — Sughrue Mion, PLLC

(57) ABSTRACT

Provided is an oxygen concentration device which, as an oxygen concentration device having a reduced difference in flow rates of gas which flows through a pressure equalization valve of a pressure equalization path during a purge step and a pressure equalization step, is provided at at least one end side of the pressure equalization valve with a pressure control member having a difference in pressure loss due to the direction of gas flow so that pressure loss of the gas which flows through the pressure equalization path in one direction becomes nearly equal to that of the gas which flows therethrough in the opposite direction.

4 Claims, 5 Drawing Sheets

(52) U.S. Cl.
CPC ..... *B01D 53/0423* (2013.01); *B01D 53/0446* (2013.01); *B01J 20/3491* (2013.01); *C01B 13/027* (2013.01); *C01B 13/0259* (2013.01); *A61M 2202/0208* (2013.01); *A61M 2205/3341* (2013.01); *B01D 2256/12* (2013.01); *B01D 2257/102* (2013.01); *B01D 2259/40028* (2013.01); *B01D 2259/40035* (2013.01); *B01D 2259/4533* (2013.01)

(58) Field of Classification Search
CPC ............... B01J 20/3491; B01D 53/047; B01D 53/0446; B01D 53/0423; B01D 2256/12; B01D 2257/102; B01D 2259/40028; B01D 2259/40035; B01D 2259/4533; C01B 13/0259; C01B 13/027
USPC ................. 95/130; 96/121, 143; 128/205.12, 128/205.24
See application file for complete search history.

(56) References Cited

U.S. PATENT DOCUMENTS

| | | | | |
|---|---|---|---|---|
| 5,258,056 A | * | 11/1993 | Shirley | B01D 53/047 95/138 |
| 5,474,595 A | * | 12/1995 | McCombs | B01D 53/0415 95/130 |
| 5,518,526 A | * | 5/1996 | Baksh | B01D 53/0476 95/100 |
| 5,871,564 A | * | 2/1999 | McCombs | A61M 16/0666 95/98 |
| 2012/0272966 A1 | | 11/2012 | Ando et al. | |

FOREIGN PATENT DOCUMENTS

| | | |
|---|---|---|
| JP | 2008-264064 A | 11/2008 |
| JP | 2011-020566 A | 2/2011 |
| JP | 2012-085934 A | 5/2012 |
| WO | 2013/134645 A1 | 9/2013 |
| WO | 2014/051158 A1 | 4/2014 |

OTHER PUBLICATIONS

Communication dated Aug. 17, 2017, from European Patent Office in counterpart application No. 15845486.8.
International Search Report of PCT/JP2015/077408 dated Nov. 2, 2015.
Communication dated Oct. 3, 2017 from the Japanese Patent Office in counterpart application No. 2016-550432.

* cited by examiner (8-1)

801
802
803
804
805

(8-2)

OXYGEN CONCENTRATION DEVICE

CROSS REFERENCE TO RELATED APPLICATIONS

This application is a National Stage of International Application No. PCT/JP2015/077408 filed Sep. 17, 2015, claiming priority based on Japanese Patent Application No. 2014-195031 filed Sep. 25, 2014, the contents of all of which are incorporated herein by reference in their entirety.

TECHNICAL FIELD

The present invention relates to a medical oxygen concentration device which provides users such as patients having respiratory disease with oxygen-enriched air, and to a pressure equalization orifice which cancels out a difference in pressure loss due to the difference in the gas flow direction in the pressure equalization path, the difference in pressure loss being particularly problematic when generating oxygen by a pressure-swing adsorption method.

BACKGROUND ART

In recent years, the number of patients suffering from respiratory system diseases such as asthma, pulmonary emphysema, chronic bronchitis and the like has tended to increase. One of the most effective therapeutic methods for these diseases is oxygen inhalation therapy. In such oxygen inhalation therapy, oxygen gas or oxygen-enriched gas is inhaled by patients. An oxygen concentration device, liquid oxygen or oxygen gas cylinder, and the like are known as an oxygen supply source used for the oxygen inhalation therapy. However, an oxygen concentration device is mainly used in home oxygen therapy because it is convenient to use and easy for maintenance and management.

An oxygen concentration device is a device to supply oxygen to a user by separating and concentrating oxygen that makes up 21% of the air. As such device, there are a membrane-type oxygen concentration device that uses a membrane which selectively permeate oxygen and a pressure swing adsorption-type oxygen concentration device that uses an adsorbent which can preferentially adsorbs nitrogen or oxygen. A pressure swing adsorption-type oxygen concentration device is mainly used because it can obtain highly concentrated oxygen of 90% or more.

The pressure swing adsorption-type oxygen concentration device continuously produces a highly concentrated oxygen gas by repeating alternately an adsorption step and a desorption step. In the former step, un-adsorbed and concentrated oxygen gas is obtained by supplying air compressed by a compressor to a plurality of adsorption cylinders filled with an adsorbent, such as 5A, 13X, or Li—X type molecular sieve zeolites, which selectively adsorbs nitrogen relative to oxygen and by adsorbing nitrogen under pressurized conditions. In the latter step, the adsorbent is regenerated by desorbing and purging nitrogen adsorbed on the adsorbent under a reduced pressure of atmospheric pressure or less in the adsorption cylinder. Production of further concentrated oxygen gas is realized by, in addition to the steps of absorption and desorption, using a purge step for introducing highly concentrated oxygen from the adsorption cylinder in the adsorption step into the adsorption cylinder in the desorption step and a pressure equalization step for recovering compression energy by communicating an adsorbent cylinder that has completed the adsorption step and an adsorbent cylinder that has completed the desorption step, thereby equalizing the pressure of the two cylinders.

A pressure swing adsorption-type oxygen concentration device can produce a highly concentrated oxygen gas by being equipped with a plurality of adsorption cylinders packed with an adsorbent that selectively adsorbs nitrogen rather than oxygen, a compressor that supplies compressed air to the adsorption cylinders, a flow path switching means that repeats, by sequentially switching a flow path between the compressor and each adsorption cylinder, at a prescribed timing, an adsorption step in which pressurized air is supplied to each adsorption cylinder and concentrated oxygen is taken out, a desorption step in which each adsorption cylinder is decompressed and the adsorbent is regenerated, a pressure equalization step for communicating each of the adsorption cylinders, and a purge step where the highly oxygen-concentrated gas from an adsorption cylinder at an adsorption step side is introduced to an adsorption cylinder at a desorption step side.

CITATION LIST

Patent Literature

Japanese Unexamined Patent Application Publication No. 2008-214151

SUMMARY OF INVENTION

Technical Problem

In a flow path which connects between a plurality of adsorbent cylinders, there are provided an electromagnetic valve which controls timing of step switching and an orifice(s) which controls flow rate, and purge and pressure equalization steps are conducted by flowing gas between the adsorbent cylinders at a prescribed timing. At this time, the flow rate of the gas which flows between the plurality of adsorbent cylinders is required to be of comparable level irrespective of the flow direction. However, because the electromagnetic valve provided in such a flow path (hereinafter, referred to as a pressure equalization path) has directionality and a value of pressure loss is different depending on the direction of gas flow, the flow rate of the gas which flows between the adsorbent cylinders is different depending on the flow direction, even when the amount of air supplied from a compressor to the adsorbent cylinder is the same among the plurality of adsorbent cylinders. Even though the pressure equalization path is provided with an orifice(s) to control the flow rate, the orifice structure itself also has directionality, wherein the orifice structure has both an orifice plate which constitutes the orifice and a connecting part with a piping, wherein the orifice plate is a constituent thereof. Thus, the value of pressure loss is different depending on the direction of gas flow in the pressure equalization path, and the pressure equalization path has a structure in which the gas flow rate is different depending on the flow direction.

The present invention provides an oxygen concentration device which, by controlling a difference in pressure loss in an orifice(s) and a piping mounted on an oxygen concentration device, decreases the difference in pressure loss due to the difference in the direction of gas flow when combined with an electromagnetic valve, and decreases a difference in the flow rate of gas which flows between adsorbent cylinders through a pressure equalization path during a purge step and a pressure equalization step.

The present inventors have found the following inventions to solve such problems.
1. An oxygen concentration device which generates oxygen-enriched gas, comprising: adsorbent cylinders packed with an adsorbent which preferentially adsorbs nitrogen rather than oxygen; a compressor which supplies compressed air to the adsorbent cylinders; a flow path switching valve for switching between a flow path between the compressor and the adsorbent cylinders and a flow path between the adsorbent cylinders and an exhaust pipe for discharging desorbed gas to outside of the system in order to repeat at a fixed timing an adsorption step in which compressed air is supplied to the adsorption cylinders and nitrogen in the compressed air is adsorbed to generate unadsorbed oxygen, a desorption step in which the adsorption cylinders are purged under reduced pressure to desorb the nitrogen and regenerate the adsorbent, and a pressure equalization step in which an adsorbent cylinder after completion of the adsorption step and an adsorption cylinder after completion of the desorption step are connected to each other to equalize pressure of the two cylinders; and a pressure equalization valve provided on a pressure equalization path which connects between the adsorbent cylinders,
wherein a pressure control member having a difference in pressure loss due to the direction of gas flow is provided at at least one end side of the pressure equalization valve so that pressure loss of gas which flows through the pressure equalization path in one direction becomes nearly equal to that of the gas which flows therethrough in the opposite direction.
2. The oxygen concentration device according to above clause 1, wherein the pressure control member is an orifice structure or a pipe member having a difference in pressure loss due to the direction of gas flow.
3. The oxygen concentration device according to above clause 1 or 2, wherein, at both ends of the pressure equalization valve, an orifice structure having a cylindrical member having an orifice plate facing the pressure equalization valve side and a pipe-connecting part is provided, wherein the orifice structures are composed of a combination of the orifice structure at the inlet side of the pressure equalization valve side, wherein the orifice plate at the cylindrical member side has a conically-shaped tapered part with the orifice at concavity, and the orifice structure at the outlet side of the pressure equalization side, wherein the orifice plate at the cylindrical member side has a plane-shaped part.
4. The oxygen concentration device according to any of above clauses 1 to 3, wherein a difference between pressure loss of gas which flows through the pressure equalization path in one direction and pressure loss of the gas which flows therethrough in the opposite direction is 5 kPa or less.

Advantageous Effects of Invention

According to the present invention, it is possible to provide an oxygen concentration device that can maintain a flow rate of gas that flows through a pressure equalization path provided between a plurality of adsorbent cylinders during a purge step/pressure equalization step, at about the same level irrespective of the flow direction, and continuously generates high-concentration oxygen stably.

REFERENCE SIGNS LIST

1: Oxygen concentration device, 3: user (patient), 701: power plug, 101: HEPA filter, 102: intake muffler, 103: compressor, 104: flow path switching valve, 105: adsorbent cylinder, 106: pressure equalization valve, 107: orifice, 108: check valve, 109: product tank, 110: pressure control valve, 111: flow rate setting means, 112: particle filter, 201: humidifier, 301: oxygen concentration sensor, 302: flow rate sensor, 303: pressure sensor, 401: control means, 501: compressor box, 502: cooling fan, 503: exhaust muffler, 801: sleeve, 802: coil, 803: plunger, 804: valve element, 805: valve seat

[Description of Embodiments]

Constitution of the present invention will be described in the following using drawings.

Figure 1:
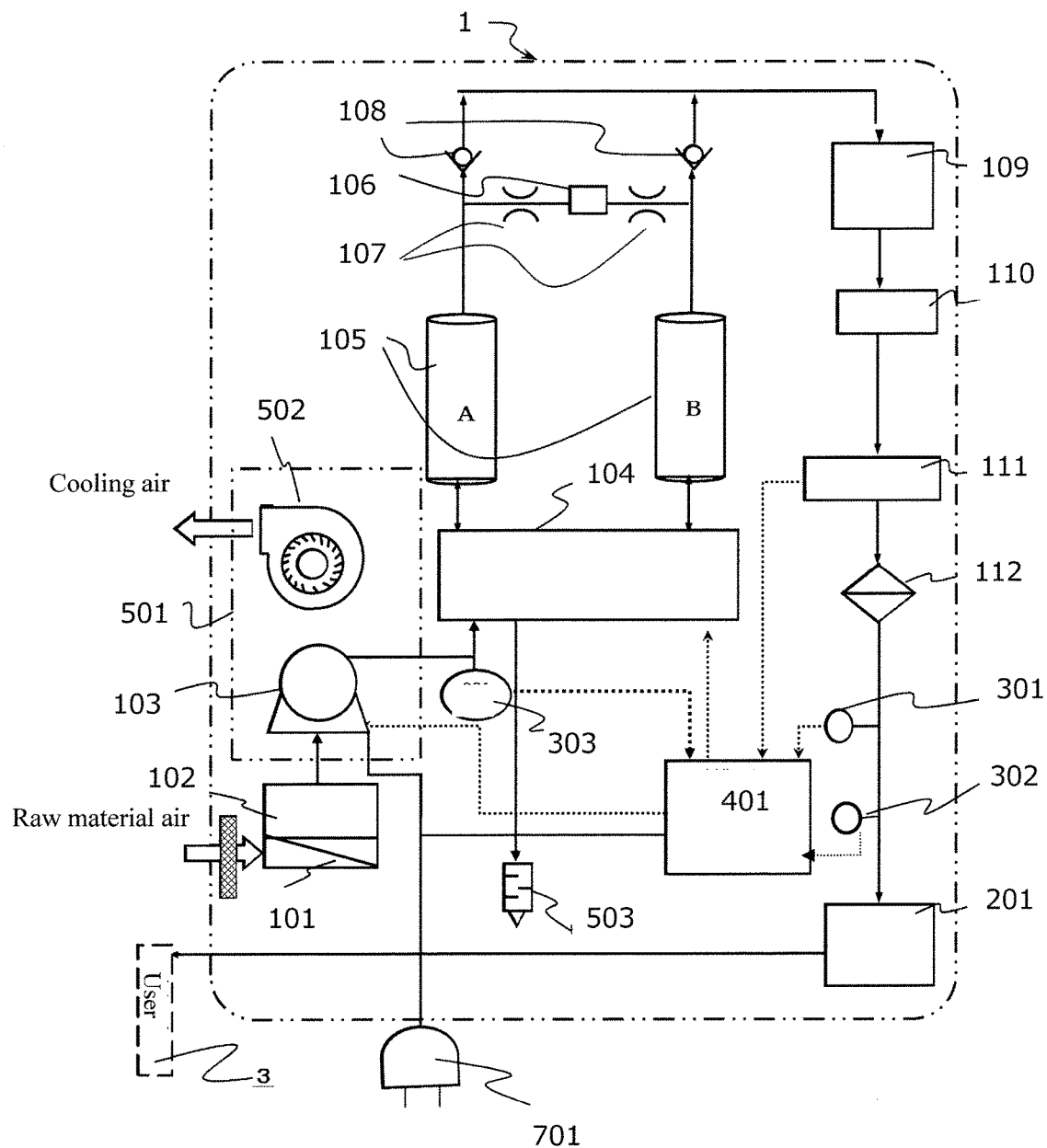
FIG. 1 shows a schematic block diagram of a pressure-swing adsorption type oxygen concentration device of an example of an embodiment of the present invention.

FIG. 1 is a schematic block diagram of a device illustrating a pressure-swing adsorption type oxygen concentration device according to one embodiment of the present invention. In this FIGS. 1, 1 and 3 respectively represent an oxygen concentration device and a user (patient) who inhales humidified oxygen-enriched air. The pressure-swing adsorption type oxygen concentration device 1 comprises an outside air intake filter 101, an intake muffler 102, a compressor 103, a flow path switching valve 104, an adsorbent cylinder 105, a pressure equalization valve 106, an orifice 107, a check valve 108, a product tank 109, a pressure control valve 110, a flow rate setting means 111, and a particle filter 112. By this, it is possible to produce oxygen-enriched air containing concentrated oxygen gas from raw material air which is taken in from outside. Further, in a housing of the oxygen concentration device, there are incorporated a humidifier 201 for humidifying the oxygen-enriched air generated; a control means 401 which controls the compressor and the flow path switching valve by using a set value of the flow rate setting means 111 and values measured by an oxygen concentration sensor 301, a flow rate sensor 302, and a pressure sensor 303; a compressor box 501 for reducing noises of the compressor; and a cooling fan 502 for cooling the compressor.

First, the raw material air to be taken in from outside is introduced through an air intake port equipped with an outside air intake filter 101 for eliminating foreign matter such as dust and the like and an intake muffler 102. At this time, normal air contains about 21% oxygen gas, about 77% nitrogen gas, 0.8% argon gas, and 1.2% of gas including water vapor and others. In such a device, only oxygen gas that is necessary as respiration gas is enriched and taken out from the air .

To take out this oxygen gas, the raw material air is compressed by the compressor 103 and is supplied to an adsorbent cylinder 105 packed with an adsorbent composed of zeolite and the like, which selectively adsorbs nitrogen molecules rather than oxygen molecules, while sequentially switching the target adsorbent cylinder by means of the flow path switching valve 104, whereby about 77% nitrogen gas contained in the raw material air is selectively adsorbed and removed in the adsorbent cylinder.

The adsorbent cylinder is formed of a cylindrical container packed with the adsorbent, and usually there are used a one-cylinder type, a two-cylinder type shown in FIG. 1 using an absorption cylinder A and an absorption cylinder B and, in addition, a multi-cylinder type which includes three or more cylinders. However, in order to produce the oxygen-enriched gas continuously and efficiently from the raw material air, it is preferable to use two or more adsorbent cylinders. Furthermore, as the compressor 103, there is used a swing type air compressor and, in addition, there are cases when a rotation type compressor is used, such as a screw type, a rotary type, a scroll type, and the like. Further, a power source of an electric motor for driving the compressor may be either alternating current or direct current.

The oxygen-enriched air containing the oxygen gas, which was not adsorbed by the adsorbent cylinder 105, flows into the product tank 109 via the check valve 108 which is installed to prevent the oxygen-enriched gas from flowing back into the adsorbent cylinder.

Furthermore, the nitrogen gas adsorbed by the adsorbent packed in the adsorbent cylinder needs to be desorbed from the adsorbent in order for the adsorbent to adsorb nitrogen gas again from newly introduced raw material air. For this purpose, the adsorption cylinder is switched from a compressed state realized by the compressor to a depressurized state (for example, an atmospheric pressure state or a negative pressure state) by means of a flow path switching valve, thereby desorbing the nitrogen gas which has been adsorbed and regenerating the adsorbent.

In order to recover compression energy, product ends of an adsorbent cylinder immediately after completion of the adsorption step and an adsorbent cylinder immediately after completion of the desorption step are communicated to each other by opening/closing of the pressure equalization valve 106 to equalize pressure of the two cylinders and recover pressure energy. Further, in order to improve desorption efficiency in the desorption step, there may be provided a purge step in which the oxygen-enriched air is flowed back as a purge gas from the product end of an adsorbent cylinder in the adsorption step. At this time, in order to control the flow rate of gas that flows through the pressure equalization valve, at a constant value, the pressure equalization valve 106 is provided with an orifice structure 107 at both ends thereof.

Usually, loud gas flow noise is generated when nitrogen is desorbed and, therefore, a nitrogen exhaust muffler 503 is generally used.

The oxygen-enriched air generated from the raw material air is stored in the product tank 109. This oxygen-enriched air stored in the product tank 109 contains a high concentration, for example 95%, of oxygen gas and is supplied to the humidifier 201 while a supply flow rate and pressure thereof are being controlled by the pressure control valve 110, the flow rate setting means 111, and the like, and the humidified oxygen-enriched air is supplied to a patient. As such a humidifier, there may be used a non-water supply type humidifier which takes in moisture from outside air and supplies the same to the oxygen-enriched air in a dry state, a bubbling type humidifier which uses water, or a surface evaporation type humidifier.

Furthermore, an air quantity supplied to the adsorbent cylinder is controlled by detecting a set value of the flow rate setting means 111 and by controlling the rotation speed of the electric motor of the compressor by means of the control means 401. When the set flow rate is low, the amount of generated oxygen is suppressed and power consumption can be reduced by decreasing the rotation speed.

In the case of the two-cylinder type oxygen concentration device, gas is flowed in the purge step and the pressure equalization step from the adsorbent cylinder A to the adsorbent cylinder B or from the adsorbent cylinder B to the adsorbent cylinder A by opening the pressure equalization valve 106. In order to control the flow rate, an orifice is provided between the pressure equalization valve 106 and the adsorbent cylinder A and between the pressure equalization valve and the adsorbent cylinder B.

Figure 2:
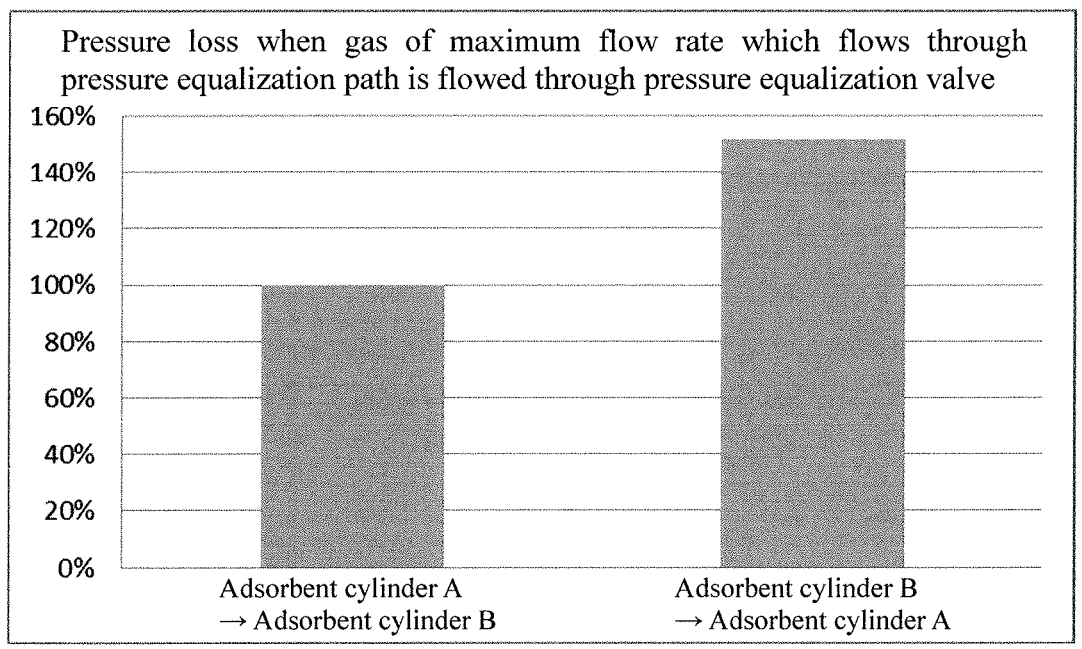
FIG. 2 shows a difference in pressure loss in a pressure equalization valve alone.
Figure 8:
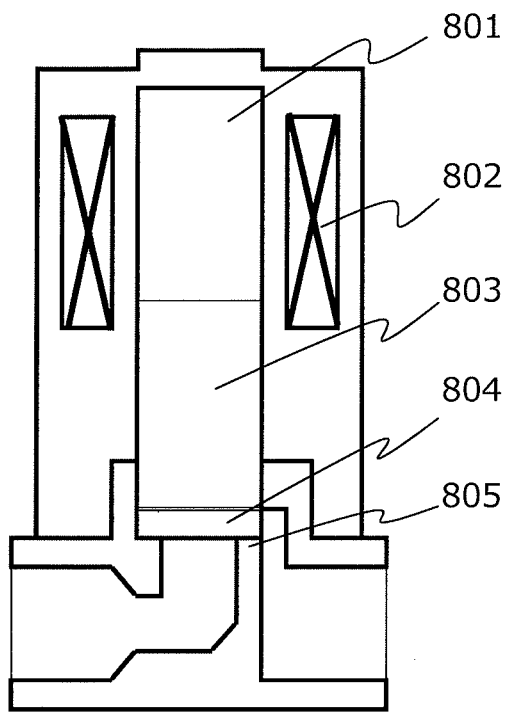
FIG. 8 shows a cross-sectional schematic diagram of a direct-acting poppet valve, which is a pressure equalization valve.
Figure 8:
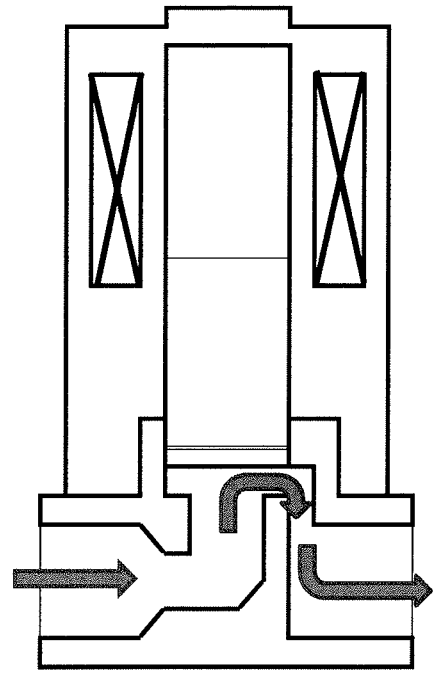

As the pressure equalization valve 106 which controls opening and closing of a pressure equalization flow path which adjusts pressure between the adsorbent cylinders of the two-cylinder type oxygen concentration device, there is frequently used a small size direct-acting poppet valve such as shown in FIG. 8. As shown in FIG. 8-2, a flow path structure of the valve part at an inlet side of the gas flow path is different from that at a outlet side thereof and, in the pressure equalization valve 106, the structure of the flow path through which the gas flows from the inlet side to the outlet side and that of the flow path through which the gas flows from the outlet side to the inlet side are asymmetrical. Therefore, when the pressure equalization valve is installed so that the inlet side of the pressure equalization valve attaches to the adsorbent cylinder A side and the outlet side of the pressure equalization valve attaches to the adsorbent cylinder B side, the value of pressure loss is different depending on the direction in which the gas flows, as shown in FIG. 2. Usually, such an electromagnetic valve is manufactured on the premise that it is used for opening and closing control of a flow path of gas which flows in one direction. Therefore, when gas is flowed in both forward and opposite directions of the electromagnetic valve, a difference is generated in pressure loss, and even if the same pressure is exerted on both ends of the electromagnetic valve, there is generated a difference in gas flow rates due to the direction in which the gas flows through the pressure equalization path.

As shown in FIG. 2, when gas is flowed through a pressure equalization valve at a maximum flow speed of the pressure equalization valve of an oxygen concentration device, pressure loss when the gas is flowed from the adsorbent cylinder B to the adsorbent cylinder A becomes as much as 152%, relative to the pressure loss which is defined as 100% when the gas is flowed from the adsorbent cylinder A to the adsorbent cylinder B. This indicates that pressure loss is less when the gas is flowed from the adsorbent cylinder A to the adsorbent cylinder B. Therefore, when oxygen is generated by switching pressure between the adsorbent cylinders in the pressure-swing adsorption method, even if the same amount of raw material air is supplied from the compressor to each adsorbent cylinder and the same pressure difference is generated between the adsorbent cylinders, the gas flows more easily in the direction from the adsorbent cylinder A to the adsorbent cylinder B than in the direction from the adsorbent cylinder B to the adsorbent cylinder A, resulting in a different gas flow rate. Therefore, a measure is being taken to control the gas flow rate by installing an orifice at both ends of the pressure equalization valve.

Figure 3:
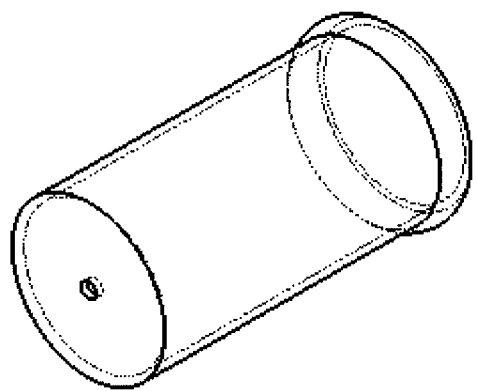
FIG. 3, FIG. 4, and FIG. 5 respectively show an outline of an orifice structure, a cross-sectional outline of an orifice structure, and a cross-sectional outline of a pressure equalization valve structure.

An orifice structure provided at both ends of the pressure equalization valve has an appearance of a cylinder such as shown, for example, in FIG. 3, wherein one end of the cylinder is provided with an orifice plate having an orifice, and at the other end with a connection part with a piping, and an inner part with a cylindrical member. Even though the orifice structure is preferably press-fit into the pipe between the pressure equalization valve and the adsorbent cylinder, connection of the pressure equalization valve and the orifice structure may be made possible by forming thread grooves on an outer surface of an end part of the orifice side, and the pipe connection part may have a structure provided with a connection part such as a one-touch joint and the like.

Figure 4:
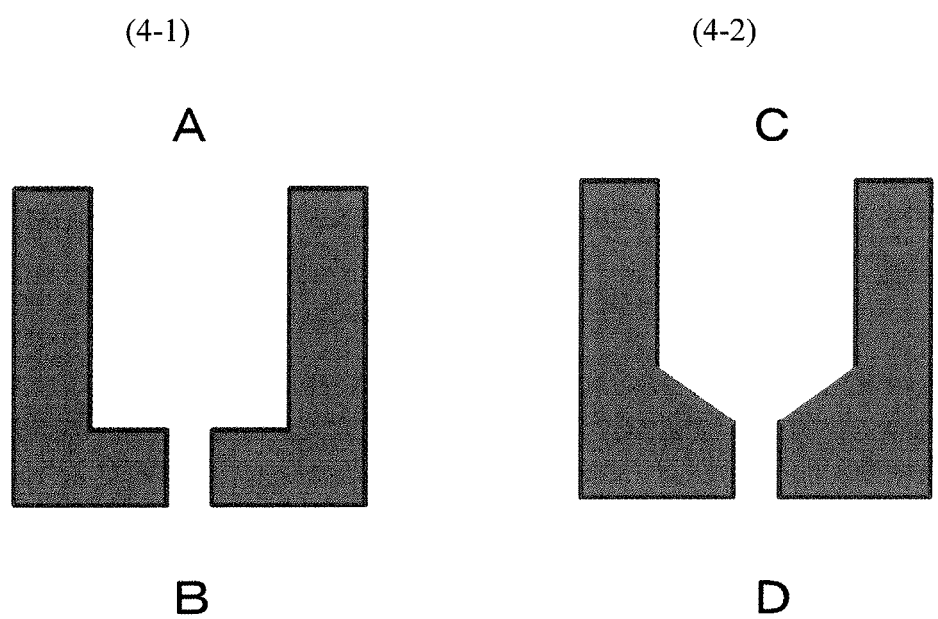

The orifice structure, as shown by cross sectional shapes of FIG. 4, has configurations provided with an orifice plate (FIG. 4-1) having a cylindrical orifice in the center of a circular plate and with an orifice plate (FIG. 4-2) having a conical concavity centering around the orifice at the center of a circular plate. Thus, a difference in pressure loss is generated due to the direction of gas flow because the shape of the orifice structure is asymmetric as shown by differences in the diameter and shape of the pipe at both sides of the orifice and a difference in the shape of the orifice itself.

In the case of the orifice structure of FIG. 4-1, pressure loss in the direction from A to B is larger than that in the opposite direction because of the difference in the diameter at both sides of the orifice. Thus, when there is the same pressure difference between A and B, the flow rate becomes larger when gas is flowed from B to A than when the gas is flowed in the opposite direction. The orifice structure of FIG. 4-2 is similarly asymmetrical and, therefore, a difference in the pressure loss is generated, and the flow rate becomes larger when gas is flowed in the direction from D to C than when the gas is flowed in the direction from C to D. When the two orifice structures are compared, pressure loss becomes smaller and flow rate becomes higher when gas is flowed in the direction from D to C of the orifice structure of FIG. 4-2 than when the gas is flowed in the direction from B to A of the orifice of FIG. 4-1.

Figure 6:
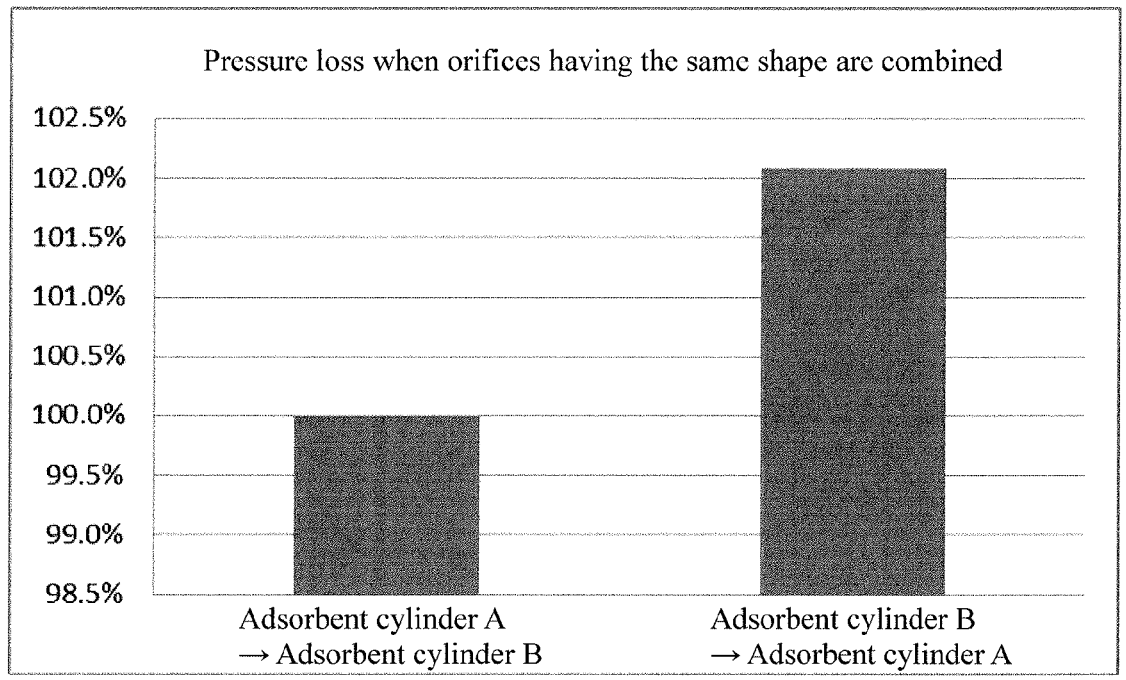
FIG. 6 shows a difference in pressure loss in a pressure equalization path provided with orifices with the same shape and FIG. 7 shows a difference in pressure loss in a pressure equalization path provided with orifices of different shapes.

When the same orifice structure is attached to both ends of the pressure equalization valve, the difference in pressure loss in the orifice due to the flow direction are canceled and, as a result, the difference in pressure loss in the pressure equalization valve cannot be resolved. For example, when the orifice structure of FIG. 4-2 is used at both ends of the pressure equalization valve, a difference in flow rates of the electromagnetic valve cannot be cancelled. Therefore, when the orifice structures are mounted on a pressure equalization path including the pressure equalization valve 106 and the orifice 107 of the oxygen concentration device shown in FIG. 1, the difference in pressure loss is such that, as shown in FIG. 6, the pressure loss from the adsorbent cylinder B to the adsorbent cylinder A becomes 102.1% relative to the pressure loss of 100% when gas flows from the adsorbent cylinder A to the adsorbent cylinder B. Thus, the oxygen supply flow rate remains different depending on the flow direction of the gas. Installation of the orifice results in absolutely higher pressure loss when gas is flowed at a maximum flow speed through the pressure equalization path, and invites decrease in oxygen concentration and destabilization of oxygen concentration. It is important to bring the difference in pressure loss to zero for increasing the generated oxygen concentration and stabilizing the oxygen concentration supplied.

A combination of orifices having different shapes, rather than orifices having the same shape, enables control of variation of the difference in pressure loss due to the combination of orifices in a smaller range. In order to control the oxygen concentration at 90% or more in product gas generated, it is preferable to control the difference in pressure loss in the pressure equalization valve structure within 5 kPa. In order to maintain the oxygen concentration of the product gas at 93% or more, it is preferable to control the difference in pressure loss in a pressure equalization valve structure at 1 kPa or less or, if possible, in such a way that the difference approaches zero.

Figure 5:
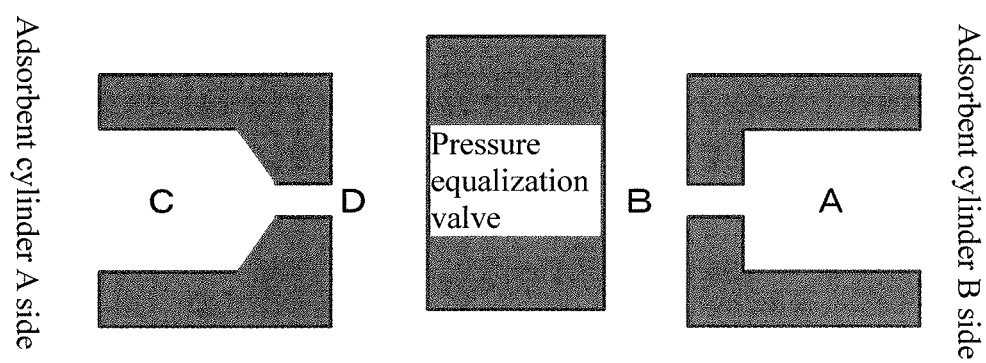

According to an example of an embodiment of the oxygen concentration device of the present invention, the device is provided with orifice structures having different shapes as shown in FIG. 4-1 and FIG. 4-2 at respective ends of the electromagnetic valve such as the one shown in FIG. 5. By arranging the direction of the orifices so that gas can flow more easily through the orifice in the direction of the pressure equalization device in which the gas is hard to flow, a configuration is obtained where a difference in pressure loss in the orifice structures in the direction of gas flow and a difference in pressure loss in the pressure equalization valve cancel each other.

Figure 7:
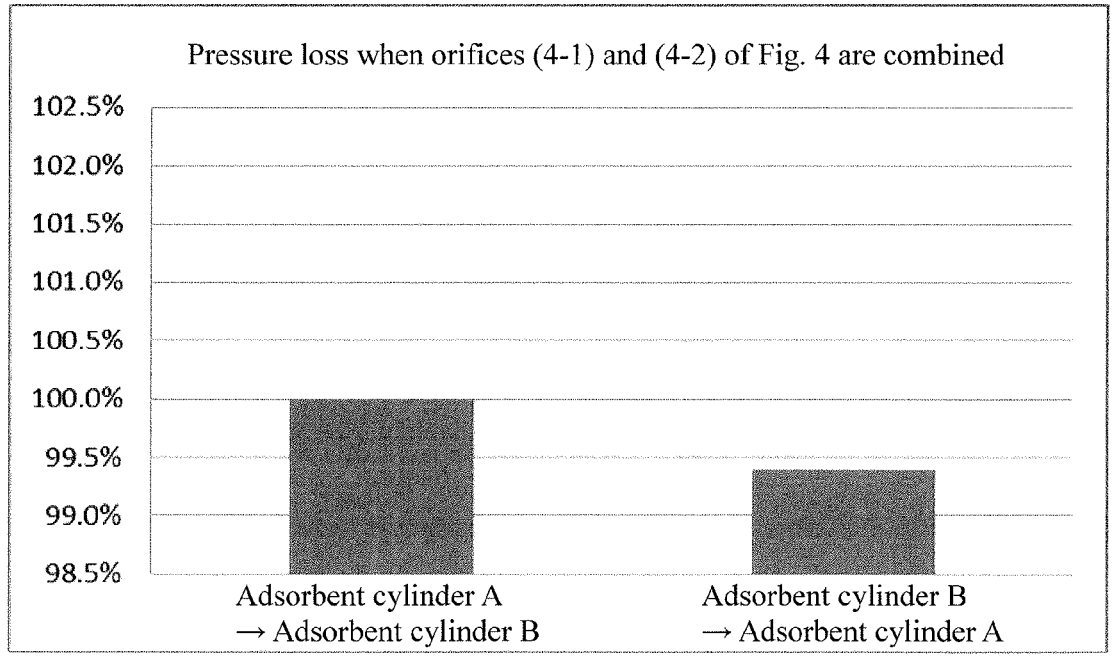

As is shown in FIG. 7, the difference in pressure loss due to the direction of gas flow through the pressure equalization path is designed so that, relative to a pressure loss of 100% when the gas flows from the adsorbent cylinder A to the adsorbent cylinder B, that from the adsorbent cylinder B to the adsorbent cylinder A becomes 99.4%, the same level as the former with a difference of 1% or less. Thus, whether gas is flowed from the adsorbent cylinder A to the adsorbent cylinder B or from the adsorbent cylinder B to the adsorbent cylinder A, the same amount of gas flows.

In the above example of an embodiment, there was illustrated an oxygen concentration device provided with an orifice structure at at least one end side of a pressure equalization valve, the orifice structure being provided as a pressure control member, which generates a difference in pressure loss due to the direction of gas flow, so that pressure loss of the gas which flows through a pressure equalization path in one direction becomes nearly equal to that of the gas which flows therethrough in the opposite direction. However, if the difference in pressure loss can be controlled, control by a difference in the pipe shape of the pipe member of the pressure equalization path and the like is also possible.

[Relationship between Difference in Pressure Loss of Pressure Equalization Valve Structure and Oxygen Concentration]

Regarding the pressure equalization valve structure having an orifice 107 provided each at both ends of a pressure equalization valve 106, four levels of pressure equalization valve structures, each having different value of difference in pressure loss due to the direction of gas flow through the pressure equalization path, were prepared and incorporated in the pressure equalization path of the oxygen concentration device described in FIG. 1 in a forward direction and in an opposite direction. The device having a total of eight levels of difference in pressure loss was subjected to measurements of oxygen concentration in the oxygen-enriched gas generated as a product gas.

TABLE 1

| Example | Difference in pressure loss in pressure equalization valve structure (kPa) | Oxygen concentration in product gas (%) |
| --- | --- | --- |
| 1 | −5.4 | 90.0 |
| 2 | −3.3 | 91.0 |
| 3 | −2.5 | 91.7 |
| 4 | −0.4 | 93.1 |
| 5 | +0.4 | 92.7 |

TABLE 1-continued

| Example | Difference in pressure loss in pressure equalization valve structure (kPa) | Oxygen concentration in product gas (%) |
|---|---|---|
| 6 | +2.5 | 91.9 |
| 7 | +3.3 | 90.6 |
| 8 | +5.4 | 89.8 |

When pressure loss in the pressure equalization structure due to the direction of gas flow is the same, that is, when the difference in pressure loss is zero, the oxygen concentration of the product gas becomes maximum and, by selecting the orifices so that the difference in pressure loss becomes less than 5 kPa, an oxygen concentration of 90% or more can be maintained.

INDUSTRIAL APPLICABILITY

In the oxygen concentration device of the present invention, stable generation of oxygen can be realized by providing a pressure equalization path, which is set up so that a difference in pressure loss between adsorbent cylinders is eliminated by selecting a combination of an orifice structure(s) and a pressure equalization valve, thereby decreasing a difference in flow rates.

The invention claimed is:

1. An oxygen concentration device which generates oxygen-enriched gas, comprising: adsorbent cylinders packed with an adsorbent which preferentially adsorbs nitrogen rather than oxygen; a compressor which supplies compressed air to the adsorbent cylinders; a flow path switching valve for switching between a flow path between the compressor and the adsorbent cylinders and a flow path between the adsorbent cylinders and an exhaust pipe for discharging desorbed gas to outside of the system in order to repeat at a fixed timing an adsorption step in which compressed air is supplied to the adsorption cylinders and nitrogen in the compressed air is adsorbed to generate unadsorbed oxygen, a desorption step in which the adsorption cylinders are purged under reduced pressure to desorb the nitrogen and regenerate the adsorbent, and a pressure equalization step in which an adsorbent cylinder after completion of the adsorption step and an adsorption cylinder after completion of the desorption step are connected to each other to equalize pressure of the two cylinders; and a pressure equalization valve provided on a pressure equalization path which connects between the adsorbent cylinders, wherein a pressure control member having a difference in pressure loss due to the direction of gas flow is provided at at least one end side of the pressure equalization valve so that pressure loss of gas which flows through the pressure equalization path in one direction becomes nearly equal to that of the gas which flows therethrough in the opposite direction.

2. The oxygen concentration device according to claim 1, wherein the pressure control member is an orifice structure or a pipe member having a difference in pressure loss due to the direction of gas flow.

3. The oxygen concentration device according to claim 1, wherein, at both ends of the pressure equalization valve, an orifice structure having a cylindrical member having an orifice plate facing the pressure equalization valve side and a pipe-connecting part is provided, wherein the orifice structures are composed of a combination of the orifice structure at the inlet side of the pressure equalization valve side, wherein the orifice plate at the cylindrical member side has a conically-shaped tapered part with the orifice at concavity, and the orifice structure at the outlet side of the pressure equalization side, wherein the orifice plate at the cylindrical member side has a plane-shaped part.

4. The oxygen concentration device according to claim 1, wherein a difference between pressure loss of gas which flows through the pressure equalization path in one direction and pressure loss of the gas which flows therethrough in the opposite direction is 5 kPa or less.

* * * * *